US00PP25690P3

(12) United States Plant Patent
Scalzo et al.

(10) Patent No.: US PP25,690 P3
(45) Date of Patent: Jul. 14, 2015

(54) BLUEBERRY PLANT NAMED 'BLUE SILK'

(50) Latin Name: *Vaccinium corymbosum*
Varietal Denomination: Blue Silk

(71) Applicant: The New Zealand Institute for Plant and Food Research Limited, Auckland (NZ)

(72) Inventors: Jessica Scalzo, Havelock North (NZ); Narandra Patel, Hamilton (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 85 days.

(21) Appl. No.: 13/815,545

(22) Filed: Mar. 8, 2013

(65) Prior Publication Data

US 2013/0347150 P1 Dec. 26, 2013

Related U.S. Application Data

(60) Provisional application No. 61/664,156, filed on Jun. 26, 2012.

(51) Int. Cl.
*A01H 5/08* (2006.01)
*A01H 5/00* (2006.01)

(52) U.S. Cl.
USPC ..... Plt./157
CPC ..... *A01H 5/00* (2013.01)

(58) Field of Classification Search
USPC ..... Plt./157
CPC ..... A01H 5/08; A01H 5/00; A01H 5/0887
See application file for complete search history.

(56) References Cited

U.S. PATENT DOCUMENTS

| | | | |
|---|---|---|---|
| PP20,515 | P3 | 12/2009 | Patel |
| PP21,720 | P3 | 2/2011 | Patel |
| PP21,721 | P3 | 2/2011 | Patel |
| PP21,735 | P3 | 3/2011 | Patel |
| PP21,736 | P3 | 3/2011 | Patel |
| PP21,761 | P3 | 3/2011 | Patel |
| PP21,881 | P3 | 4/2011 | Patel |

*Primary Examiner* — June Hwu
(74) *Attorney, Agent, or Firm* — Lathrop & Gage LLP

(57) ABSTRACT

A new and distinct blueberry variety is described. The variety results from selection among a population of seedlings derived from the controlled cross of the varieties 'Elliott' (not patented) and 'Puru' (U.S. Plant Pat. No. 6,701). The new variety is distinguished from others by its late seasonality, fruit size, and plant habit. Fruit of 'Blue Silk' is medium-large in size with a medium-strong bloom.

4 Drawing Sheets

Genus and species of plant claimed: *Vaccinium corymbosum.*

Variety denomination: 'Blue Silk'.

BACKGROUND TO THE INVENTION

Seeds obtained from the deliberate crossing of the varieties 'Elliott' (not patented), female parent, and 'Puru' (U.S. Plant Pat. No. 6,701), male parent, which occurred at Ruakura, Hamilton, New Zealand were shipped to Gilten, Germany. Seedlings obtained from this cross were planted out in Gilten, Germany in 2002. Three seedlings were selected from this family in 2004, one of which was given the breeder code 'ZDM035'. In the Northern Hemisphere summer of 2008 'ZDM035' was identified as having potential as a new variety and in 2009 it was asexually propagated. The resulting plants were planted out at Gilten and were subsequently found to be true to type demonstrating that the characteristics of the new variety are stable and transmitted without change through succeeding generations. Asexual propagation has since been carried out through both soft and hard wood cuttings in Gilten, Germany. 'ZDM035' was later designated 'Blue Silk'. 'Blue Silk' is distinguished from its parents, 'Elliot' and 'Puru', as fruit bloom is heavier than both parents. 'Blue Silk' fruit is harvested mid-late season while 'Puru' is early season and Elliot late season.

SUMMARY OF THE INVENTION

Blue Silk' is characterised by its mid-late seasonality, fruit size, bloom, and upright habit. 'Blue Silk' is distinguished from a number of other varieties by the following characteristics:

'Blue Silk' is harvested significantly later than 'Bluecrop' (not patented) grown in Gilten, Germany. Fruit of 'Blue Silk' have been observed to be starting to turn blue when approximately 50% of the 'Bluecrop' crop has been harvested.

'Blue Silk' produces medium to large fruit, averaging 2.2 g, whereas 'Nui' (U.S. Plant Pat. No. 6,699) produces large fruit, averaging 3 g, which reach harvest maturity earlier, under the same conditions in Germany.

DETAILED DESCRIPTION

Figure 1:
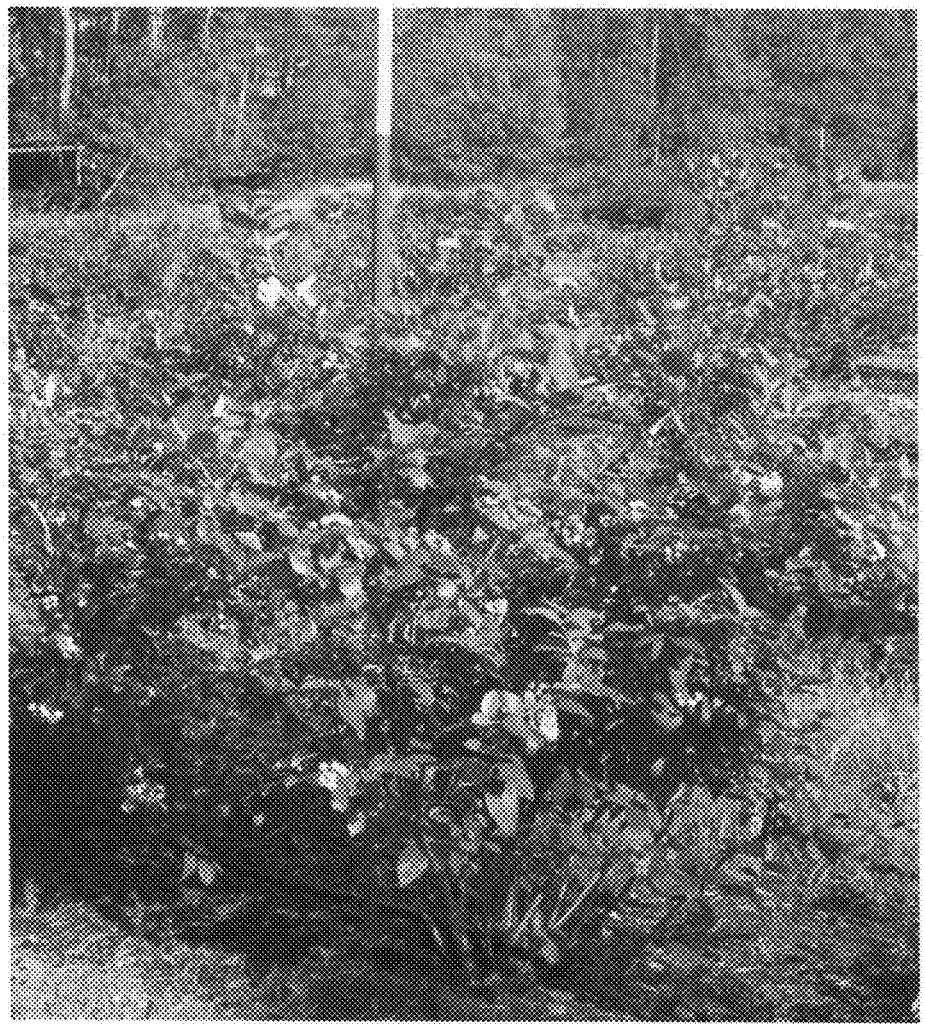
FIG. 1 shows a mature, six year old 'Blue Silk' plant.
Figure 2:
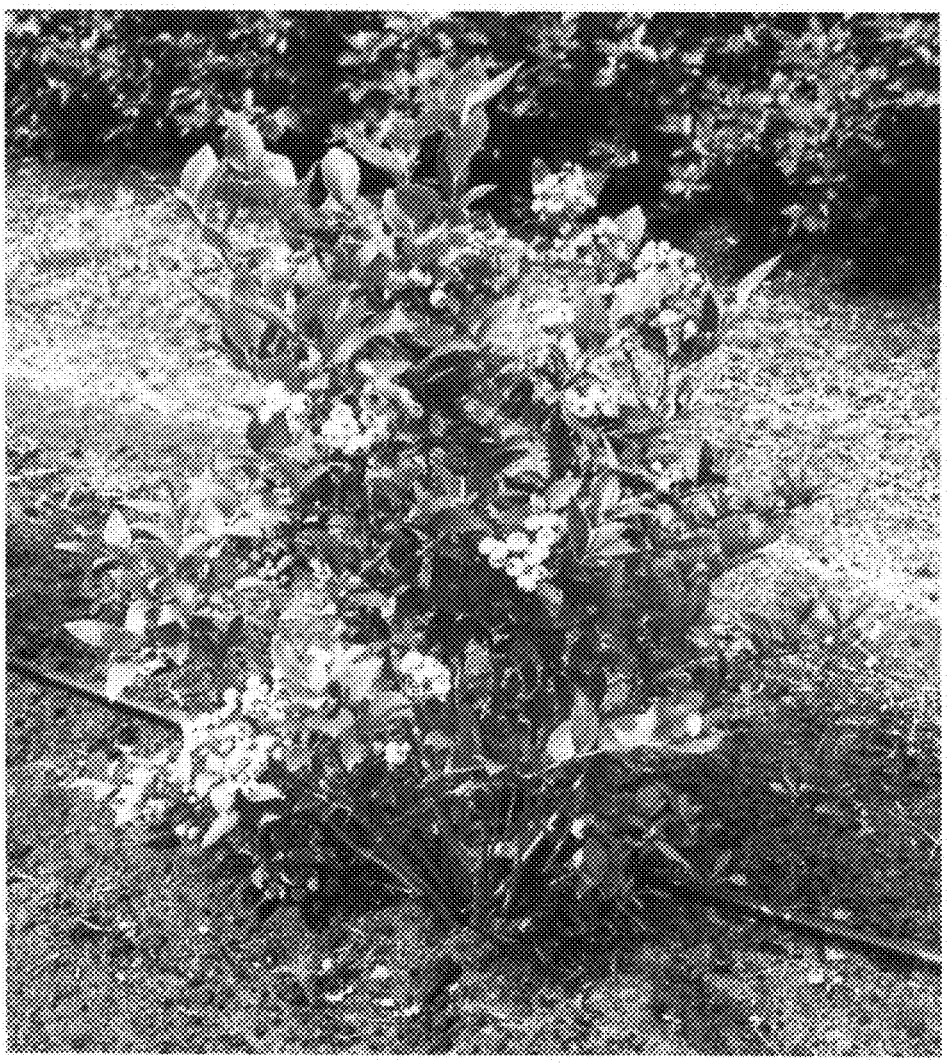
FIG. 2 shows a juvenile, two year old plant.
Figure 3:
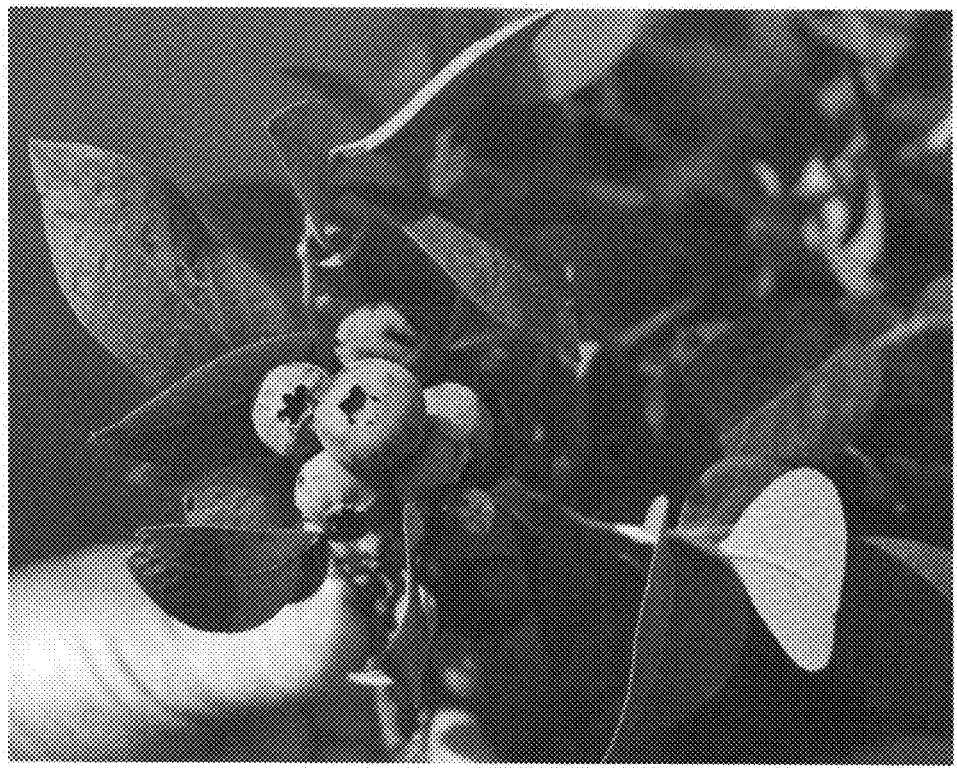
FIGS. 3 and 4 show show fruit of 'Blue Silk' on the plant.
Figure 4:
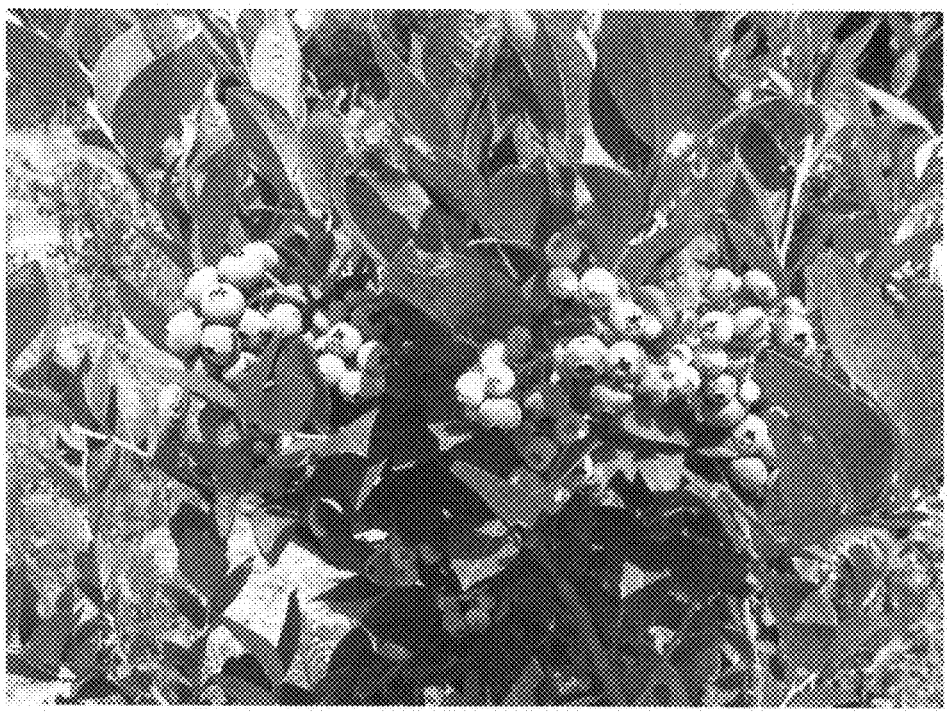

The following is a description of the new variety with color terminology in accordance with The Royal Horticultural Society Colour Charts (R.H.S.C.C.) 2001 edition.

The specimens described were grown in Gilten, Germany. The observations were made in the 2010-2014 seasons on 4-8 year old bushes.

Plant and foliage:

*Plant*.—Medium size at maturity, with an average plant height of 1.2 m and average canopy diameter of 1.1 m, managed under standard orchard practice. Growth habit is upright and fruit are borne only on one-year-old shoots. The surface texture of 6 month old dormant stems is smooth and the colour near yellow green 144D.

*Leaves*.—Mature fully expanded leaves are an average of approximately 78.0 mm long and 37.2 mm wide. The pinnate leaves are oval to oblong in shape with smooth margins. The leaves are coloured near yellow green 146A with a moderate and uniform glossiness on the upper surface. On the lower surface the leaves are near coloured green 138C and venation coloured near greyed purple 185B. The petioles are an average of approximately 2.3 mm long and coloured near yellow green 145B.

Infloresence:

*Flower*.—The flower shape is urceolate and has an average length of 11.7 mm. The average style length is 9.5 mm. The tip of the style is lower than the corolla tip. The ovary is inferior. The petals are fused into the corolla tube and have 5 lobes. The corolla surface texture is smooth and coloured near white 155D. The average corolla tube diameter is 6.1 mm. The average number of flowers per cluster is 13. The calyx colour is near yellow green 144B with anthocyanin blush at tips.

Fruit:

*Immature fruit*.—Coloured near yellow green 145C.

*Mature fruit*.—Medium to large in size, firm, with an average fresh weight of 2.5 g and diameter of 18.0 mm. The fruit have a medium to strong bloom. The fruit skin colour with bloom is near violet blue 97B and after the bloom is removed is near blue 103A. The fruit are generally oblate in shape with a small moist scar, on average 1.3 mm long, and have an average brix of 14.2% at maturity. The average diameter of the calyx aperture is 5.5 mm and the depth of the calyx basin 2.1 mm. The calyx aperture on the ripe berry is star shaped. The flesh colour is near greyed green 193D. The average number of berries per cluster is 13.

*Seeds*.—There is an average of between 3 and 6 seeds per fruit with an average length of 1.8 mm, coloured near greyed-orange N170A.

Events: The timing of the beginning of flowering is medium compared to standard *V. corymbosum* varieties, while the timing of the beginning of fruit ripening is mid-late—similar to that of 'Elizabeth' (not patented).

Pest and disease: 'Blue Silk' does not appear particularly resistant or susceptible to any particular pests or diseases known to afflict *V. corymbosum*.

Hardiness: The plant cold hardiness according to the American zone classification has not been determined. 'Blue Silk' has a chilling requirement of between 800-1000 hours.

The invention claimed is:

1. A new and distinct blueberry plant substantially as illustrated and described herein.

* * * * *